(12) United States Patent
Frisén et al.

(10) Patent No.: US 7,279,332 B2
(45) Date of Patent: *Oct. 9, 2007

(54) METHOD OF ISOLATING EPENDYMAL NEURAL STEM CELLS

(75) Inventors: Jonas Frisén, Stockholm (SE); Ann Marie Janson, Stockholm (SE); Clas Johansson, Stockholm (SE); Stefan Momma, Spånga (SE); Diana Clarke, Stockholm (SE); Ming Zhao, Solna (SE); Urban Lendahl, Sundbyberg (SE); Kioumars Delfani, Solna (SE)

(73) Assignee: NeuroNova AB, Stockholm (SE)

( * ) Notice: Subject to any disclaimer, the term of this patent is extended or adjusted under 35 U.S.C. 154(b) by 420 days.

This patent is subject to a terminal disclaimer.

(21) Appl. No.: 10/326,438

(22) Filed: Dec. 20, 2002

(65) Prior Publication Data

US 2003/0129747 A1   Jul. 10, 2003

Related U.S. Application Data

(63) Continuation of application No. 09/104,772, filed on Jun. 25, 1998, now Pat. No. 6,541,247.

(51) Int. Cl.
*C12N 5/00* (2006.01)
*C12N 5/02* (2006.01)
*C12N 5/08* (2006.01)

(52) U.S. Cl. .................... 435/375; 435/325; 435/368

(58) Field of Classification Search ............. 435/368, 435/375, 383, 384, 325
See application file for complete search history.

(56) References Cited

U.S. PATENT DOCUMENTS

| | | | |
|---|---|---|---|
| 5,753,505 A | 5/1998 | Luskin | 435/375 |
| 5,753,506 A | 5/1998 | Johe | 435/377 |
| 5,851,832 A | 12/1998 | Weiss et al. | 435/368 |
| 6,541,247 B1 * | 4/2003 | Frisen et al. | 435/325 |
| 2003/0092176 A1 | 5/2003 | Jansen et al. | |

FOREIGN PATENT DOCUMENTS

| | | |
|---|---|---|
| WO | WO94/02593 | 2/1994 |
| WO | WO95/13364 | 5/1995 |
| WO | WO97/09885 | 3/1997 |
| WO | WO97/11716 | 4/1997 |
| WO | WO97/44442 | 11/1997 |
| WO | WO99/16863 | 4/1999 |

OTHER PUBLICATIONS

Weiss and van der Kooy (1998) CNS stem cells: Where's the biology (a.k.a. beef)? J. Neurobiology 36: 307-314.*

Date, 1996, Parkinson's Disease, Trophic Factors, and Adrenal Medullary Chromaffin Cell Grating: Basic and Clinical Studies, *Brain Research Bulletin* 40(1):1-19.

Goldman et al., 1998, Strategies utilized by migrating neurons of the postnatal vertebrate forebrain, *TINS* 21(3):107-114.

Hagan et al., 1997, "Parkinson's disease: prospects for improved drug therapy," *TiPS* 18:156-163.

McKay, 1997, "Stem Cells in the Central Nervous System," *Science* 276:66-71.

Mehta et al., 1997, "Neural Transplantation in Parkinson's Disease," *Can. J. Neurol. Sci.* 24:292-301.

Morrison et al., 1997, "Regulatory Mechanisms in Stem Cell Biology," *Cell* 88:287-298.

Reynolds and Weiss, 1992, "Generation of Neurons and Astrocytes from Isolated Cells of the Adult Mammalian Central Nervous System", *Science* 255:1707-1710.

Alvarez-Buylla et al. Primary neural precursors and intermitotic nuclear migration in the ventricular zone of adult canaries. J Neurosci. Feb. 1, 1998;18(3):1020-37.

Alvarez-Buylla and Lois , Neuronal stem cells in the brain of adult vertebrates. Stem Cells. May 1995;13(3):263-72. Review.

Higuchi et al. Differential expression of Notch1 and Notch2 in developing and adult mouse brain. Brain Res Mol Brain Res. Apr. 1995;29(2):263-72.

Lindsell et al. Expression patterns of Jagged, Delta1, Notch1, Notch2, and Notch3 genes identify ligand-receptor pairs that may function in neural development. Mol Cell Neurosci. 1996;8(1):14-27.

Vogel G. Cell biology. Stem cells: new excitement, persistent questions. Science. Dec. 1, 2000;290(5497):1672-4.

Weiss et al. Multipotent CNS stem cells are present in the adult mammalian spinal cord and ventricular neuroaxis. J Neurosci. Dec. 1, 1996;16(23):7599-609.

U.S. Appl. No. 09/719,001, filed Jul. 12, 2001, Jansen et al. (National Stage of PCT/SE99/01157).

* cited by examiner

*Primary Examiner*—Anne-Marie Falk
(74) *Attorney, Agent, or Firm*—Jones Day

(57) ABSTRACT

The present invention relates to a method of determining whether a test compound is a proliferation-inducing or proliferation-inhibiting agent of ependymal neural stem cells. The method comprises: (a) contacting an ependymal neural stem cell with the test compound: and (b) determining the proliferation of the ependymal neural stem cell, wherein if the proliferation of the ependymal neural stem cell is increased in the presence of the test compound as compared to the absence of the test compound, the test compound is identified as a proliferation-inducing agent or wherein if the proliferation of the ependymal neural stem cell is decreased in the presence of the test compound as compared to the absence of the test compound, the test compound is identified as a proliferation-inhibiting agent.

3 Claims, 13 Drawing Sheets

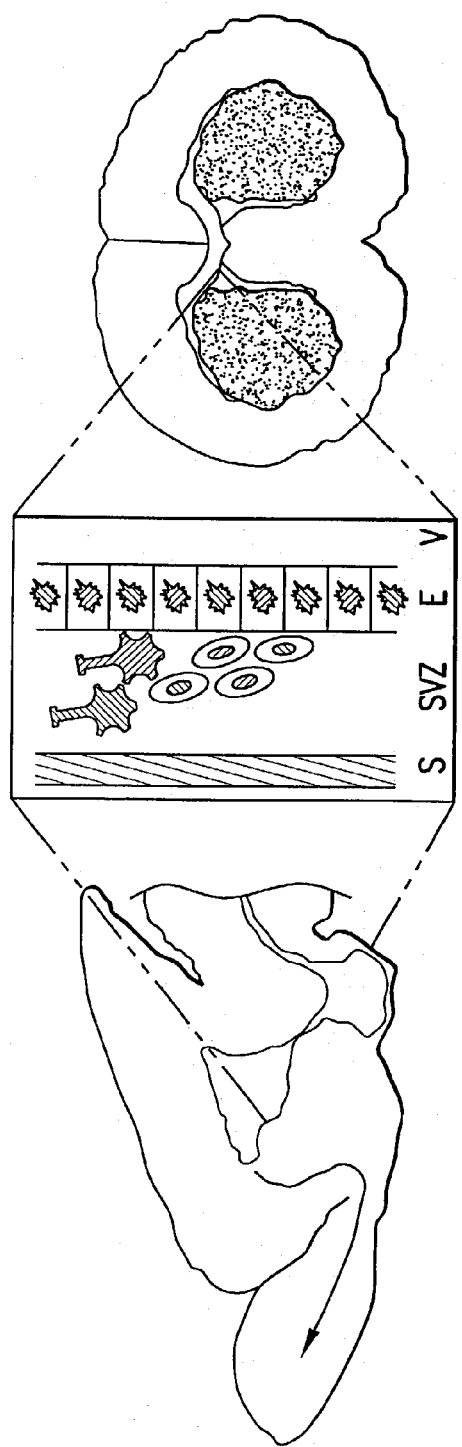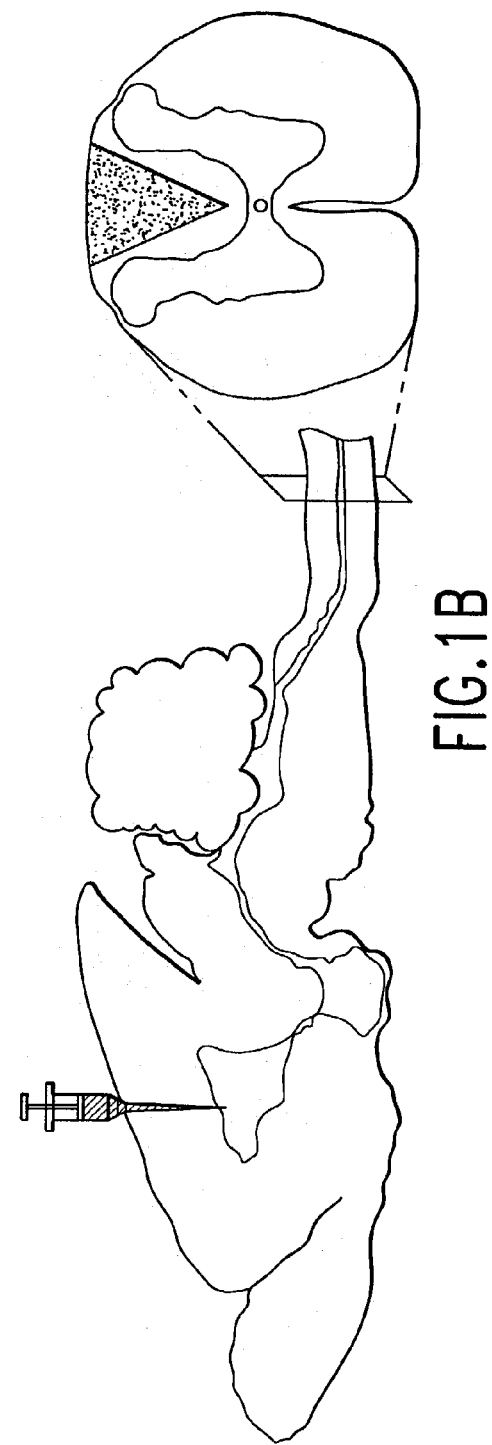

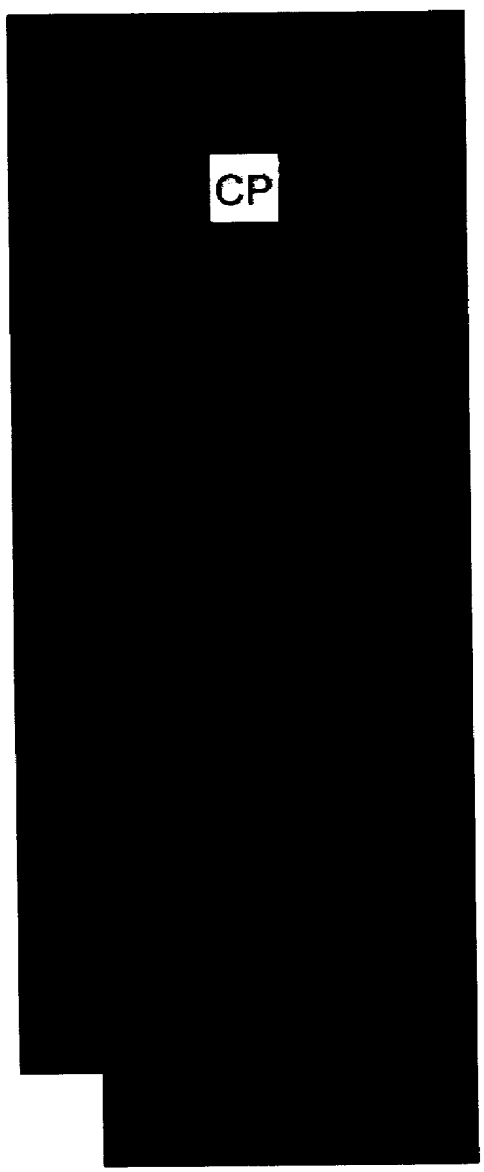
FIG. 1D
FIG. 1E
FIG. 1C

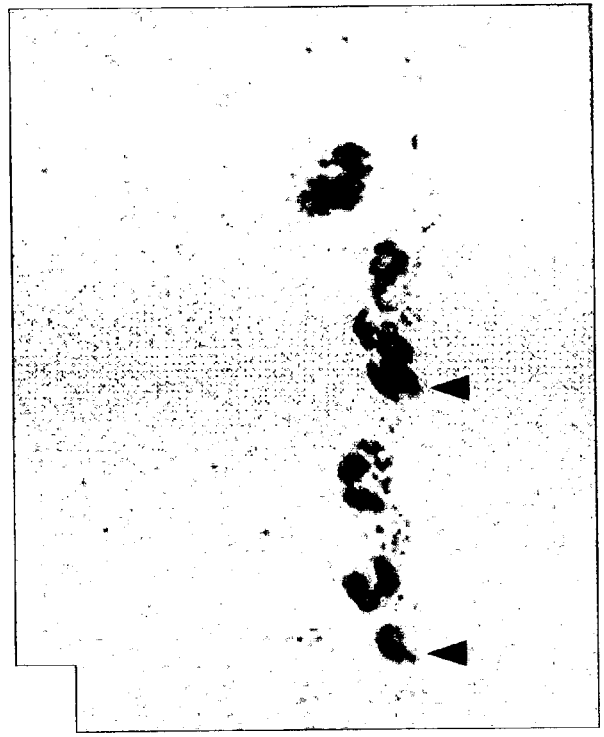
FIG.4A  FIG.4B
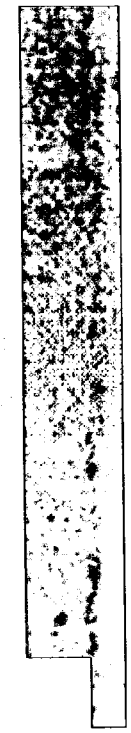
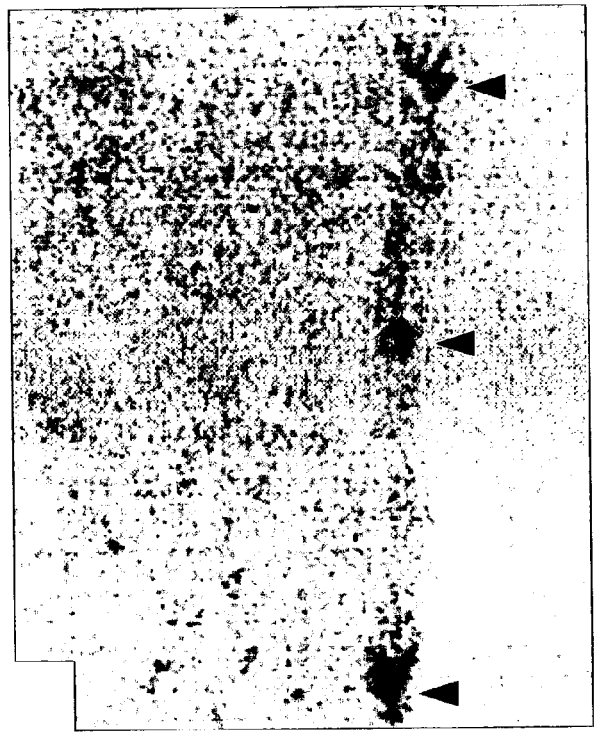
FIG.4C  FIG.4D

METHOD OF ISOLATING EPENDYMAL NEURAL STEM CELLS

This is a continuation of prior application Ser. No. 09/104,772 filed Jun. 25, 1998 now U.S. Pat. No. 6,541,247.

TECHNICAL FIELD

The present invention relates to a method of isolating cells that have never before been identified and located from the mammalian central-nervous system. The invention also relates to such isolated cells per se and to various uses thereof as well as assays using the same.

BACKGROUND

Until recent years, a 'static' view on the fate of nerve cells in the central nervous system (CNS) was universally prevailing, based on the assumption that new neurons could not be generated in the adult mammalian brain. However, such renewal of neurons has been described in certain regions of the adult CNS, e.g. in the olfactory bulb, where signals from neurons from the organ of smell reach the brain (Kaplan et al., Science 197:1092) and in the dentate gyrus of hippocampus (Bayer et al., Science 216:890). Since neurons are unable to divide, the addition of new neurons suggested the existence of immature cells, i.e. progenitor or stem cells, which may generate neurons. Evidence supporting the existence of a multipotent neural stem cell in the adult mammalian CNS was presented a few years ago (Reynolds et al., Science 255:1707). However, as in several other organs, the realization of the existence of a stem cell has come before identifying and localizing the same. Interestingly, neurogenesis in the adult brain persists throughout adulthood in rodents (Kuhn P G, J. Neurosci. 16:20) and seems to be an evolutionary well conserved phenomenon present in a variety of mammals (Gould et al. J. Neurosci. 17:2492, Gould et al., Proc. Natl. Acad. Sci. USA 95:3168). In humans, the issue is difficult to address, although experimental data from cultures of adult human brain tissue (Kirschenbaum et al, Cereb. Cortex 6:576) suggest that there may be continuous neurogenesis also in the adult human CNS.

The existence of neural stem cells in the adult mammalian CNS was first demonstrated by culturing cells from the adult rat brain and spinal cord. Under certain culture conditions a population of multipotent neural stem cells can be propagated from dissociated adult rat brain and spinal cord (Reynolds et al., Science 255:1707, Dev. Biol. 175:1, Weiss et al., J. Neurosci. 16: 7599). The culture medium has to contain a mitogenic factor, e.g. epidermal growth factor (EGF) or fibroblast growth factor (FGF), and serum must be excluded. In contrast to stem cells, most other CNS cell types do not survive in these cultures.

Under these conditions, single cells proliferate in vitro and the progeny forms a cluster of aggregated cells (Reynolds et al., Science 255:1707, Dev. Biol. 175:1). Such cell clones detach from the culture dish after a few days in vitro. The cells continue to proliferate and form a characteristic spheroid cell aggregate, referred to as a neurosphere, of tightly clustered cells, all of which are derived from a single cell. Most of the cells in the neurosphere express nestin, an intermediate filament found in neuroepithelial stem cells. (Lendahl et al., Cell, 60:585), but not markers typical for differentiated cells. These undifferentiated cells rapidly differentiate if plated on an adhesive substrate or if serum is added to the culture medium. Importantly, a clone of cells derived from a single cell can generate neurons, astrocytes and oligodendrocytes, demonstrating that at least the initial cell was multipotent (Reynolds et al., Science 255:1707, ibid. Dev. Biol. 175:1). Moreover, if a cell clone is dissociated, many of the cells will form new clusters of undifferentiated multipotent cells (Reynolds et al., Dev. Biol. 175:1), thus fulfilling the criteria for being stem cells.

Thus, the method above suffers from the serious drawback that the cell population used is of a complex, mixed composition. Even though it has been possible to enhance the growth of some cell types, it is impossible to draw any conclusions regarding the original localization of the cells obtained.

Consequently, other methods have been proposed to determine the localization of the adult CNS stem cells, wherein different parts of the adult rodent forebrain have been carefully dissected and cultured to test for the capacity of neurogenesis. These studies have demonstrated that stem cells are most abundant in the wall of the lateral ventricle and in the hippocampus (Lois et al., Proc. Natl. Acad. Sci. USA, 90:2074, Morsehead et al., Neuron 13:1071, Palmer et al., Mol. Cell. Neurosci. 6:474, ibid, 8:389). Furthermore, stem cells can be isolated from the walls of the third and fourth ventricles as well as from the adult spinal cord, suggesting the presence of stem cells adjacent to the ventricular system along the entire neuraxis (Weiss et al., J. Neurosci. 16: 7599).

However, the exact localization and identity of the neural stem cell has been enigmatic. The wall of the lateral ventricles has been the subject of detailed morphological studies (Doetsch et al., J. Neurosci. 17:5046). The ventricular system is lined by a single layer of ependymal cells. Mammalian ependymal cells have traditionally been considered to be highly specialized cells with the main function to form a barrier between the nervous tissue and the cerebrospinal fluid (Del Bigio, Glia 14:1), which strongly argues against these cells being undifferentiated stem cells. Beneath the ependymal layer is the subependymal layer, also known as the subventricular zone. This area harbors astrocytes, neuroblasts and progenitor cells (Doetsch et al., J. Neurosci. 17:5046). The progenitor cells in the subependymal layer have a high proliferation rate (Morsehead et al., J. Neurosci. 12:249). Generally, stem cells proliferate very slowly and when the rapidly proliferating subependymal cells were selectively killed, the stem cell population was not depleted, arguing against these cells being the stem cells (Morsehead et al., Neuron 13:1071).

WO 97/44442 (Johe) discloses isolation of stem cells from the CNS of mammals and more specifically from the subependymal region of striatum lining the lateral ventricles. However, only subependymal cells are used and thus there is no further teaching regarding the identity and role of mammalian ependymal cells that alters the conventional one.

WO 95/13364 (Weiss, et al.) relates to a method of proliferation of CNS precursor, cells located by the CNS ventricle of a mammal. However, only precursor cells are disclosed, and there are no teachings regarding other cell stages, such as stem cells.

In this context, it is interesting to note that besides the olfactory bulb and the hippocampus, data on continuous neurogenesis throughout adulthood in other regions of the mammalian brain have been scarce. As an example that neurogenesis may be a more widespread phenomenon, a small number of cells with the capacity to generate neurons in vitro has been isolated from the striatum and septum (Palmer et al., Mol. Cell. Neurosci. 6:474), although it has not been tested if these cells have stem cell properties or if they are committed neuronal progenitors.

There is increasing evidence that nervous system injuries may affect stem cells in the adult CNS. After both spinal cord and brain injuries, nestin expression is increased in cells lining the central canal and in the subventricular zone, respectively (Frisén et al., J. Cell Biol. 131:453, Holmin et al. Eur. J. Neurosci. 9:65). These cells have been suggested to derive from stem cells. With time, nestin expressing cells are seen progressively further from the central canal and the lateral ventricle and these cells express astrocytic markers (Frisén et al., J. Cell Biol. 131:453, Holmin et al. Eur. J. Neurosci. 9:65). These data have lead to the suggestion that stem cells or progenitor cells residing by the ventricular system are induced to proliferate, migrate toward the site of the injury and differentiate to astrocytes. Furthermore, hippocampal lesions increase the proliferation of hippocampal progenitor cells and the number of granular neurons in the hippocampus (Gould et al. Neurosci. 80:427). However, since the stem cell has not been identified or exactly localized it is not clear whether stem cells play a role in injury processes.

Cell loss is a common factor in many types of nervous system disorders. Distinct cell types are affected in different diseases, e.g. dopaminergic neurons in Parkinson's disease, motor neurons in amyotrophic lateral sclerosis and oligodendrocytes in multiple sclerosis. Several different cell types in a certain area can be affected in other situations, such as stroke or traumatic injury. Currently, no methods are available in clinical practice to stimulate generation of new cells in the nervous system. Transplantation of cells from human embryos or animals have been tested clinically with some encouraging results. However, these methods have several problems, mainly ethical and immunological, which makes it very unlikely that they will be used in any larger number of patients.

Accordingly, the discovery of the existence of neural stem cells in the adult CNS of mammals is important and may make it possible to develop strategies to stimulate generation of new neurons or glial cells. However, several important questions have remained unanswered and better methods to culture these cells and to study them quantitatively in vivo are needed. Most importantly, it is absolutely vital to identify and localize the stem cell in the adult CNS in order to be able to study these cells further and to stimulate generation of new neurons from the stem cells.

Furthermore, there are no methods available today to purify stem cells at an early step in tissue culture. Although there are several general methods available for purifying cell populations in other tissues, it is impossible to utilize these methods, or to develop new methods, without knowledge of the true identity of the stem cell. Such methods would allow studies of a more well defined cell population and would be valuable for screening pharmaceutical compounds. Moreover, the development of quantitative methods to label and follow the stem cells and their progeny in vivo to allow detailed studies of, for example, regulation of the generation of new neurons to analyze the effect of different chemicals or genetically manipulate the stem cells are needed. Again, although there are methods known in the art that can be used to follow other cell populations in vivo, it is impossible to utilize these methods or develop new methods for following stem cells since the identity of the stem cell has been unknown. The development of quantitative methods to follow stem cells and their progeny in animal models of neurodegenerative disorders and injuries of the CNS would open up the possibility to screen new treatment strategies in human conditions where today only some of the symptoms, but not the neuronal loss per se, can be alleviated.

Thus, a problem within this field is that even though neural stem cells are known to exist, the localization and identity therof is not known. Could this be accomplished, a great step forward would be taken by research aimed at providing the above defined goals.

SUMMARY OF THE INVENTION

The object of the present invention is solve the above defined problem. More specifically, the present invention relates to a method of isolating ependymal neural stem cells from a mammalian CNS. The present identification of the stem cell has now made it possible to develop methods to purify these cells, study them quantitatively in vivo, genetically modify them and stimulate them with various pharmaceutical compounds in vitro and in vivo. Furthermore, the present invention provides evidence that the stem cells follow new migratory pathways to various neuroanatomical cell groups in the CNS and that they are able to transform into neurons in vivo. The invention also comprises an unbiased quantitative method to assess neurogenesis in various regions of the brain as well as techniques to analyze the total number of stem cells and their progeny migrating to various regions of the brain. Altogether, the developments provided by the present invention greatly increase the possibilities to develop strategies to stimulate generation of new cells in the central nervous system.

Accordingly, the actual identity and localization of ependymal neural stem cells are disclosed herein for the first time ever, thus enabling various advantageous uses and applications thereof within the medical and diagnostic field. The invention also relates to in vitro and in vivo assays, wherein the new findings according to the invention are advantageously employed.

BRIEF DESCRIPTION OF THE DRAWINGS

FIG. 1 illustrates the specific labeling of ependymal cells and is a schematic drawing of the migration of neurons in the adult forebrain and the structure of the wall of the lateral ventricle.

FIG. 4 illustrates the proliferation of ependymal cells by showing an immunohistochemical detection of 5-bromo-2'-deoxyuridine (BrdU) in the lateral wall of the lateral ventricle after two weeks continuous BrdU administration (A,B) or two weeks administration followed by one week without BrdU (C,D).

DEFINITIONS

Figure 2A:
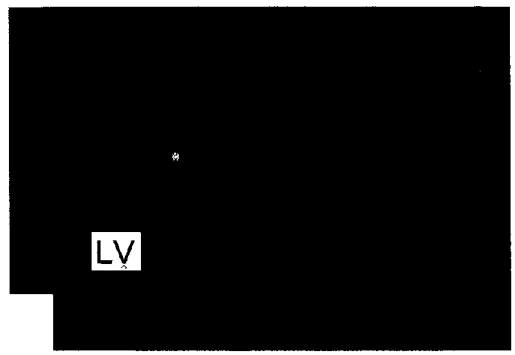
FIG. 2 illustrates the generation of olfactory bulb neurons and neurospheres.
Figure 2B:
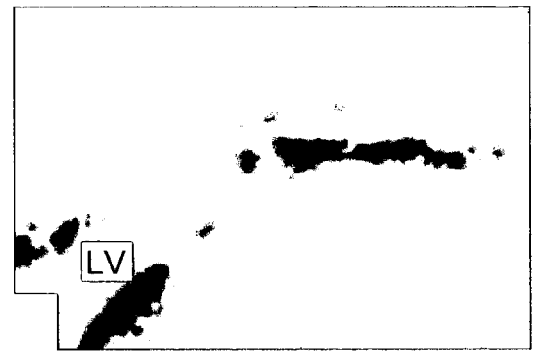
Figure 2C:
Figure 2D:
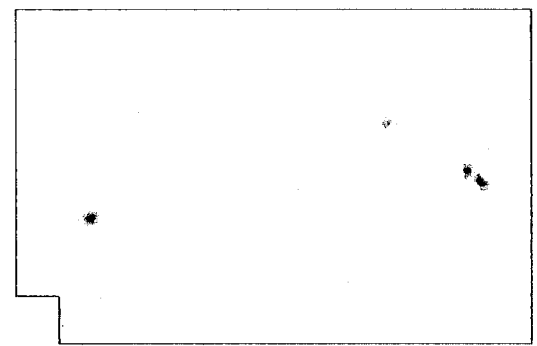
Figure 2E:
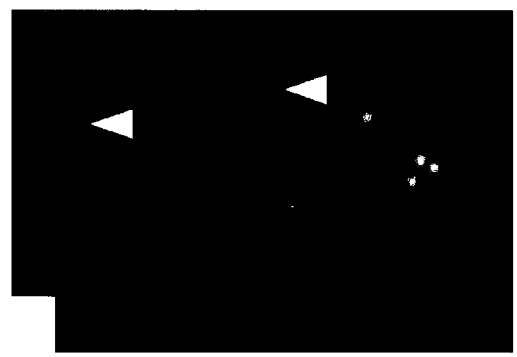
Figure 2F:
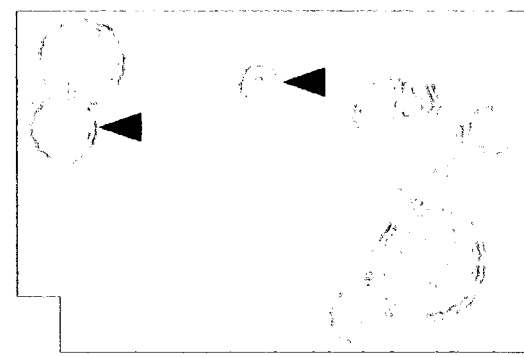

As used herein, the term "isolated" refers to cell fractions isolated from an animal, (e.g., a human, a rat, a mouse, etc.) and purified up to at least about 10%, such as 80%. Purity is measured by comparing the number of neural stem cells with the total number of cells. For example, an "80% pure" preparation of ependymal neural stem cells means that 80% of the cells in the preparation are ependymal neural stem cells. The term "neural stem cells" relates to cells capable of generating aggregates of undifferentiated cells, so called neurospheres, under suitable conditions, e.g. a medium containing appropriate mitogens. "Ependymal cells" refers to any cell originating from the ependymal layer in the CNS ventricular system or the same cell type located elsewhere. In the present context, it is to be understood that among the features that characterize the ependymal neural stem cells according to the invention is the capability thereof to generate new stem cells, precursors, progenitor cells, neurons, astroglia or oligodendroglia. The term "adult" is used herein to differentiate the neural stem cells previously identified in embryos from the present ependymal neural stem cells of the invention obtained from post-natal mammals. Thus, adult stem cells are in essence non-embryonic stem cells.

DETAILED DESCRIPTION OF THE INVENTION

More specifically, in a first aspect, the present invention relates to a method of isolating ependymal neural CNS stem cells from an animal, which method comprises the steps of
(a) screening single cells obtained by dissociating CNS tissue from said animal for cells exhibiting at least one characteristic of an ependymal neural stem cell; and
(b) recovering the cells that exhibit the characteristic or characteristics screened for in step (a).

The animal from which the cells are isolated may be a human. In an advantageous embodiment of the present method, the cells screened in step (a) are from tissue comprising the walls of the ventricular system of the brain or spinal cord, or any other area that contains ependymal cells, of said animal. The dissection and recovery of such tissue is easily performed by the skilled man in this field by any suitable routine method. The dissociation of the tissue into individual cells is performed by any suitable method, such as an enzymatic and/or mechanical treatment, and is not restricted in any way as long as the desired single cells are obtained as a result thereof. Examples of such methods are e.g. trituration, trypsin treatment, collagenase treatment and hyaluronidase treatment. Most preferably, the dissociation is performed by enzymatic treatment with trypsin. The dissociation of tissue may alternatively be performed by any other method easily chosen by the skilled man in view of the prevailing conditions.

The screening of the resulting cells is also performed by any suitable method depending on the characteristic, trait or property of an ependymal cell used. In one embodiment of the present method, the screening is performed by use of the expression of a specific cell surface marker, such as a protein. Such an expression of a surface protein may for example be the expression of the Notch1, Notch2 and/or Notch3 receptors. In the most preferred embodiment of this method, the single cells are screened for their expression of the Notch1 receptor. In an alternative embodiment of this aspect of the invention, the single cells are screened for by specifically labeling ependymal neural stem cells or ependymal cells and choosing so labeled cells. Such a labeling may be a dye and is advantageously a fluorescent labeling, such as DiI, as shown in example 1. However, in an alternative embodiment a virus, such as an adenovirus, may be used to label the cells. The labeling of cells is used extensively within research and diagnostic methods and the choice of a suitable technique is thus easily within the skill of one in the art.

In a preferred embodiment of the method according to the invention, the cells recovered from step (b) are comprised of at least about 10% of ependymal neural stem cells, such as 10-50%, e.g., about 35%, or in a preferred embodiment, up to about 90%, or most preferably an essentially pure culture of ependymal neural stem cells. Naturally, high concentrations are possible to obtain, depending on the screening method chosen. Previously, in prior art procedures, parts of a brain have been dissociated and specific growth factors have been added in order to induce growth of a specific cell type. Such procedures have never been aimed at obtaining a pure population of ependymal neural stem cells at an early step in the culture procedure, since the identity and characteristics (for example expression of specific cell surface markers) of the ependymal neural stem cell have been unknown before the present invention. Thus, in practice, the present method yields the desired concentration of a cell type, i.e. the ependymal neural stem cells disclosed herein, that has never been identified and/or localized before. In a specific embodiment, the product consists of about 90-95% of ependymal neural stem cells. In one advantageous embodiment, the product of the method is a cell fraction consisting almost entirely, that is, of about 100%, of the ependymal neural stem cells. Accordingly, the present invention also relates to isolated ependymal neural stem cells obtainable by the method according to the present invention as well as to any fraction of isolated ependymal neural stem cells.

Thus, the invention relates to an ependymal neural stem cell of post-natal or adult tissue from the CNS or the ventricular system of the brain or spinal cord. Preferably, the ependymal neural stem cell according to the present invention expresses a cell surface marker, such as a protein, and most preferably it expresses Notch1.

In a second aspect, the present invention relates to genetically modified ependymal neural stem cells. Manipulations may be performed in order to modify various properties of the cell, e.g. to render it more adapted or resistant to certain environmental conditions, to induce a production of one or more certain substances therefrom, which substances may e.g. improve the viability of the cell or alternatively may be useful as drugs or medicaments. The invention of methods to purify ependymal neural stem cells in cell culture allows for all types of genetic manipulation, for example transfection of these cells with plasmid or viral expression vectors or purification of cells from transgenic organisms or suppression of gene expression with for example antisense DNA or RNA fragments. Localization of the ependymal neural stem cell in vivo allows for alteration of gene expression in these cells in situ with for example viral vectors.

Altering the expression of genes in cells can make these cells produce a given protein of choice or can prevent the production of an unwanted protein. Manipulating the genes of cells in vitro or in vivo in accordance with the present invention may be beneficial in a wide variety of situations. For example, cells engineered to express a growth factor, cytokine, hormone or any other protein can be transplanted to individuals which may need continuous administration of such a protein to stimulate e.g. cell signaling or cell survival.

The cells will thus serve as continuous administrators of a pharmaceutical substance. Cells for such use can be genetically tailored, by e.g. transfection with plasmid or viral vectors, or the cells can be taken from transgenic organisms. Transgenic organisms comprising cells according to the present invention are also within the scope of the present invention. Furthermore, gene expression can be altered in situ in an organism by inducing ectopic gene expression with plasmid or viral vectors as well as antisense DNA or RNA fragments. Under certain conditions, it may be valuable to use cells which lack a certain gene or produces lower levels of the gene product. For example, transplantation of cells or tissues between different individuals is limited by the expression of certain proteins on the surfaces of cells which induces the host immune system reject the graft. This is a major problem, especially if the two individuals are of different species. One way to circumvent this problem is to generate genetically modified cells or animals that lack genes that induce rejection by a host immune system. Other important implications for manipulating gene expression in cells in vitro or in vivo include inducing differentiation of an undifferentiated cell toward a certain cell fate or stimulating survival of the cell by suppressing intrinsic or extrinsic cell death signals. Furthermore, by introducing certain genes it is possible to immortalize cells and generate clonal cell lines with special features. Since the identity and localization of neural stem cells in the adult central nervous system has been unknown, it has previously been difficult to modify these cells genetically, especially in vivo (for reviews of gene therapy procedures, see Anderson, *Science* 256:808; Nabel and Felgner *TIBTECH* 11:211; Mitani and Caskey *TIBTECH* 11: 162; Mulligan Science 926; Dillon *TIBTECH* 11: 167; Miller *Nature* 357:455; Van Brunt *Biotechnology* 6(10):1149; Vigne *Restorative Neurology and Neuroscience* 8:35; Kremer and Perricaudet *British Medical Bulletin* 51(1) 31; Haddada et al. in *Current Topics in Microbiology and Immunology*, Doerfler and Böhm (eds) Springer-Verlag, Heidelberg Germany; and Yu et al., Gene Therapy 1:13, each of which is incorporated herein by reference). Thus, the present invention also encompasses gene therapy methods, wherein ependymal neural stem cells are used as well as preparations intended to be used in such methods comprising the cells according to the invention. Such gene therapy methods may be used to treat and/or prevent any conditions wherein the neurons or glia in the CNS have been impaired or are defective.

In another aspect, the present invention relates to an ependymal neural stem cell for use in therapy, e.g. as a medicament. In addition, the invention also relates to the use of an ependymal neural stem cell in the preparation of a medicament for regulating the neurogenesis or gliogenesis in the central nervous system, such as the brain. Such regulation is either inducing or inhibiting and the treatment may be aimed at Parkinson's disease, Alzheimer's disease, stroke, trauma etc. In the case of glial cells, the medicament may be intended for treating multiple sclerosis and other glia related conditions. In one particular embodiment of the invention, these aspects of the invention use ependymal neural stem cells obtained by the method disclosed above, even though the invention also encompasses the uses of any ependymal neural stem cells, such as genetically modified ependymal neural stem cells, for the present purposes.

In a further aspect, the invention relates to a pharmaceutical preparation comprising at least one ependynmal neural stem cell according to the invention and a pharmaceutically acceptable carrier. The preparations according to the invention may be adapted for injection into a suitable part of the central nervous system. Such a pharmaceutical preparation comprises any suitable carrier, such as an aqueous carrier, e.g. buffered saline etc. The active composition of the present preparation is generally sterile and free of any undesirable matter. In addition, the preparations may contain pharmaceutically acceptable auxiliary substances as required to approximate physiological conditions, such as pH adjusting agents etc. The concentration of the present ependymal neural stem cell in the preparation will vary depending on the intended application thereof and the dosages thereof are decided accordingly by the patient's physician. The pharmaceutical compositions of the present invention comprise about $10^3$ to $10^9$ ependymal neural stem cells. In some preferred embodiments, the compositions comprise about $10^5$ to $10^8$ ependymal neural stem cells. In some preferred embodiments, the compositions comprise about $10^7$ ependymal neural stem cells. The stem cells used may have been isolated by the present method or any other suitable method or obtained in any other way. In a preferred embodiment, the present ependymal neural stem cell may have been genetically manipulated in order to be especially adapted for the intended use thereof. In a further aspect, the present invention also relates to an animal, such as a mouse, that comprises a genetically modified ependymal neural stem cell according to the invention. Such animals may, e.g., be useful as models in research or for the testing of drugs.

In yet a further aspect, the present invention relates to methods of using the present ependymal neural stem cells as "drug targets", preferably in in vitro assays, to stimulate or inhibit ependymal neural stem cell proliferation or differentiation into particular neuronal phenotype or glial subtype. In a particular embodiment, the invention relates to a method of screening for differentiation inducing agents, the method comprising culturing ependymal neural stem cells in vitro, exposing the cells to one or more potential differentiating agents, and assaying for one or more indicators of differentiation. Screening for inhibitors of differentiation can be performed by, for example, culturing isolated ependymal neural stem cells, exposing the cells to one or more known differentiating agents, and either before, concomitantly with, or after exposure to the differentiating agent or agents, exposing the cells to one or more potential inhibitors of differentiation and assaying for one or more indicators of differentiation.

When screening for potential proliferation inducing agents, the method may, e.g., involve culturing of isolated ependymal neural stem cells, exposing the cells to one or more potential proliferation inducing agents, and assaying for enhanced neural stem cell growth. Screening for inhibitors of proliferation can be performed by, for example, culturing isolated ependymal neural stem cells, optionally exposing the cells to one or more known proliferation inducing agents, and either before, concomitantly with, or after exposure to the proliferation inducing agent or agents, if used, exposing the cells to one or more potential inhibitors of proliferation and assaying for one or more indicators of proliferation. The present invention also relates to the substances obtained by the methods defined above.

In another aspect, the present invention relates to an unbiased quantitative or qualitative, preferably quantitative, method to assess neurogenesis and migratory streams of stem cell progeny, preferably in in vivo assays, in various regions of the brain as well as techniques to analyze the total number of stem cells and their progeny migrating to various regions of the brain. This is for the development of new screening methods, which methods are also within the scope of the present invention as defined by the appended claims.

This could be of use in diagnosing patients suffering from neurodegenerative diseases, if the development of ependymal cell markers suitable for positron emission tomography (PET), or other imaging systems able to visualize the living brain with sufficient resolution, allows the diagnosis of defective migration and/or differentiation of the stem cell progeny in human CNS. The present invention also encompasses the diagnostic use of labeled stem cells in the ependymal layer in humans. Such cells can be followed with an imaging system (e.g., by PET) to assess their migratory pattern. The cells may be labeled by, for example, DiI ventricular injection. Cells may be labeled in vitro, then injected, or labeled in vivo, as is described in the examples. Thus, the present invention also relates to kits and assays for performing such methods as well as to substances obtained by the present methods.

In a last aspect, the present invention relates to a method of treating a patient suffering from a neurodegenerative disease, which method comprises the administration to said patient of a pharmaceutically effective amount of ependymal neural stem cells according to the invention. The patient may be any animal, including a human. There are several potential injection sites. Thus, the cells could be injected into the nerve terminal area of the cells that degenerate in the particular neurodegenerative disorder. For example, in Parkinson's Disease, the dopamine neurons that die are situated in the midbrain in substantia nigra pars compact, but the cells can be transplanted into the nerve terminal area in the forebrain. Alternatively, they may be transplanted directly into the ventricular system, into the migratory streams of cells described in the examples below, or in the neuronal cell body region of the, cells that degenerate in the particular human neurodegenerative disorder. In general, such a method is based on administration of stem cells with an unimpaired function and ability to produce neurons or other cell types depending on the human CNS disorder. Alternatively, neurons or glial cells generated from stem cells in vitro can be administrated to the CNS. Methods for transplanting cells into the brain have been described, and are known to one of skill in the art (Widner, et al., New England J. Med., 327:1556; Wenning, et al., 1997, Ann. Neurol., 42(1):95-107; Lindvall, et al., 1994, Ann. Neurol., 35(2):172-80; Widner, et al., 1993, Acta Neurol Scand Suppl, 146:43-5; Neural Grafting in the Mammalian CNS, 1985, Bjorklund and Stenevi, eds; U.S. Pat. No. 5,650,148; International Patent Publication WO 9206702, Itukura, T., et al., 1988, J. Neurosurg. 68:955-959, each of which are incorporated herein by reference).

In an alternative embodiment, the invention relates to a method of treatment and/or prevention of neurodegenerative disorders in a human or animal patient, wherein the existing defective neural stem cells' ability to produce new neurons or migrate to the appropriate target is restored. Such a method is based on the administration of a substance that stimulates and induces the neural stem cells' native properties and capability to produce neurons. Alternatively, such a method may be based on the administration of a substance that actually inhibits the degenerative process of the neurons.

In summary, the present invention will make it possible to develop new treatment strategies in diverse diseases of the CNS, not only in diseases with a slow progression of the neurodegeneration (including Alzheimer's disease, Parkinson's disease, amyotrophic lateral sclerosis, multiple sclerosis) but also in clinical situations of acute trauma to the head or spinal cord as well as in cerebrovascular diseases. Our finding that stem cells may transform into several different neuronal phenotypes (dopamine neurons, GABA-neurons, serotonin neurons), open up possible applications beyond the above mentioned diseases, where cell loss is central to the development of the disease, into possible new areas, including depression and other mental disorders.

DETAILED DESCRIPTION OF THE DRAWINGS

FIG. 1: Specific Labeling of Ependymal Cells.
Schematic drawing of the migration of neurons in the adult forebrain and the structure of the wall of the lateral ventricle (A). The ventricle (V) is lined by ependymal cells (E). Between the ependymal layer and the striatum (S) is the subventricular zone (SVZ), where precursor cells (light blue) divide to give rise to immature neurons (dark blue). The neurons migrate to the olfactory bulb (blue arrow). (B) Labeling of ependymal cells. DiI is injected stereotaxically into a lateral ventricle, resulting in labeling of ependymal cell throughout the ventricular system. In some of these animals, an incision (gray area in the spinal cord cross section) was made in spinal cord dorsal funiculus. The DiI injection labels the ependymal layer lining the lateral ventricle (C, D) and the spinal cord central canal (E) six hours after the injection. The choroid plexus (CP) is labeled in (C).

FIG. 2: Generation of Olfactory Bulb Neurons and Neurospheres
Ten days after injection of DiI (A, C) or replication-deficient adenovirus expressing LacZ (B, D) into the contralateral lateral ventricle, labeled cells are seen in the subventricular zone (A, B) and olfactory bulb (C, D). The inset in (C) shows DiI in a βIII-tubulin-immunoreactive neuron. Bright-field (E) and fluorescence (F) micrographs showing neurospheres from the brain of an animal which had received an intraventricular DiI injection. Two very weakly labeled or unlabeled neurospheres are indicated with arrowheads.

Figure 3A:
FIG. 3 illustrates the enrichment of neural stem cells with an ependymal cell specific marker.
Figure 3B:
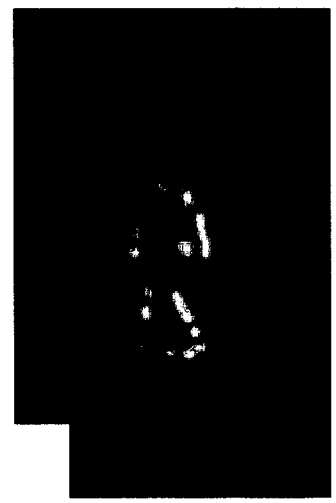
Figure 3C:
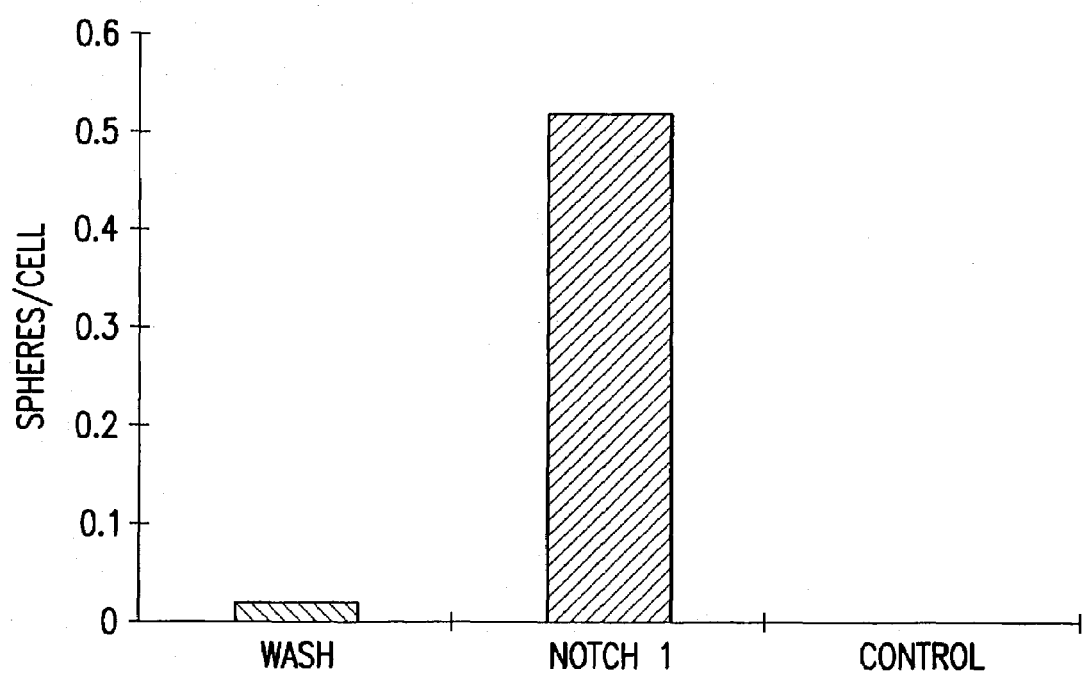
Figure 5A:
FIG. 5 discloses how the ependymal cell proliferation is induced by injury.
Figure 5B:
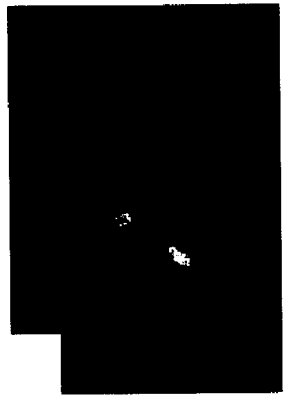
Figure 5C:
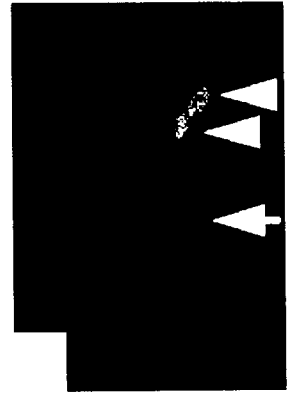
Figure 5D:
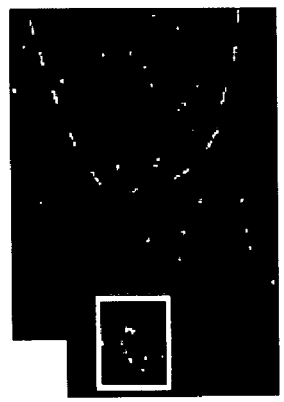
Figure 5E:
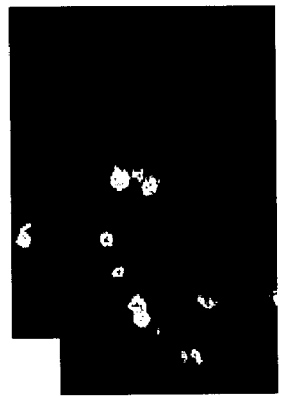
Figure 5F:
Figure 5G:
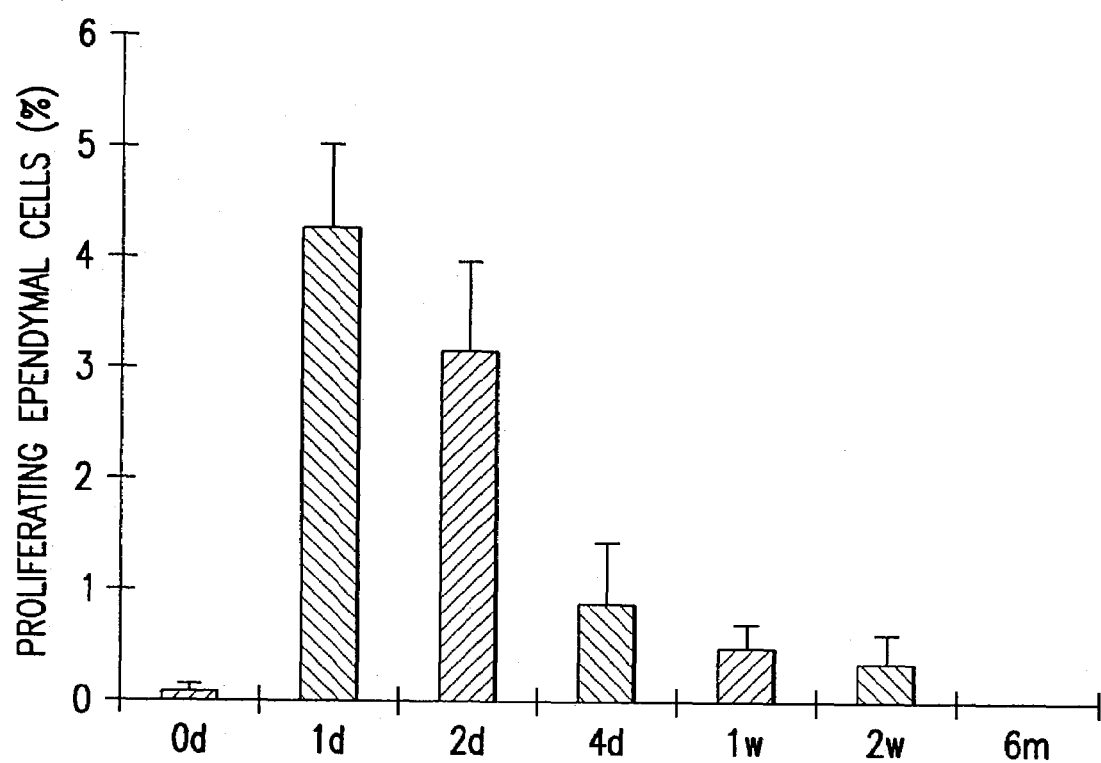
Figure 6A:
FIG. 6 shows the generation of astrocytes from ependymal cells after spinal cord injury.
Figure 6B:
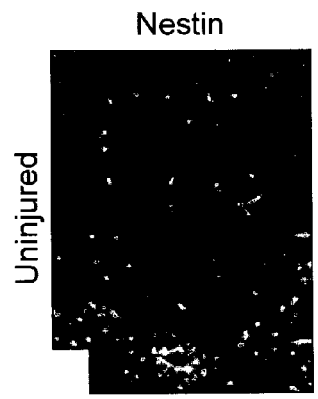
Figure 6C:
Figure 6D:
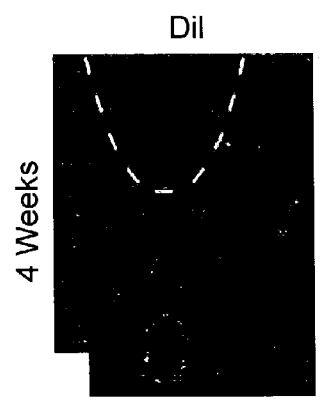
Figure 6E:
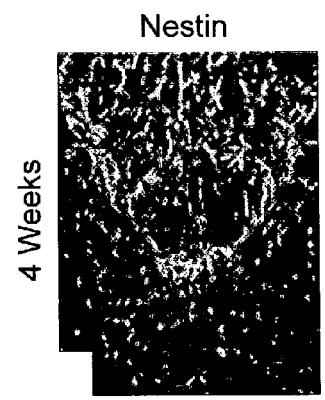
Figure 6F:
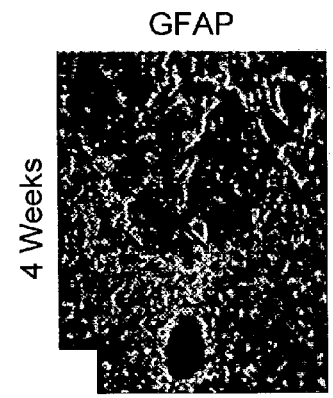
Figure 6G:
Figure 6H:
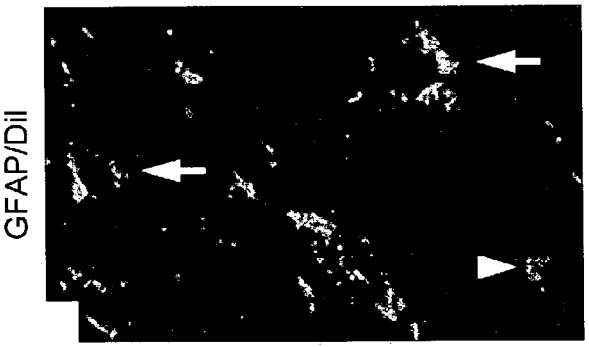

FIG. 3: Enrichment of Ependymal Neural Stem Cells with an Ependymal Cell Specific Marker
Immunofluorescence localization of Notch1 in the wall of the lateral ventricle (A) and in the spinal cord (B). Notch1 immunoreactivity is restricted to ependymal cells lining the lateral ventricle and central canal. The selective localization of Notch1 to ependymal cells enabled enrichment of ependymal cells from acutely dissociated brain and spinal cord tissue. The dissociated cells were incubated with antiserum raised against Notch1, followed by incubation with magnetic bead conjugated secondary antibodies and magnetic separation of labeled (Notch1 fraction) and unlabeled cells (wash fraction). In control experiments, the primary antiserum was omitted. The number of cells in each fraction was calculated and the number of neurospheres generated in the different cultures was counted (C).

FIG. 4: Proliferation of Ependymal Cells
Immunohistochemical detection of BrdU in the lateral wall of the lateral ventricle after two weeks continuous BrdU administration (A, B) or two weeks administration followed by one week without BrdU (C, D). (B) and (D) show details from (A) and (C), respectively. Labeled ependymal cells are indicated with arrowheads in (B) and (D).

FIG. 5: Ependymal Cell Proliferation is Induced by Injury
Immunohistochemical detection of BrdU in the spinal cord after 8 hours (A, D-F) or two weeks administration (B, C) of BrdU. (G) Proportion of spinal cord ependymal cells incorporating BrdU administered during the last 8 hours before sacrifice (BrdU labeled nuclei/total number of ependymal cell nuclei visualized with propidium iodide, n=3-5 rats at each time point, error bars show SEM).

FIG. 6: Generation of Astrocytes from Ependymal Cells after Spinal Cord Injury Distribution of DiI, nestin- and GFAP-immunoreactivity in the spinal cord. The animal in (D-F) was subjected to a dorsal funiculus incision 4 weeks prior to analysis. All animals received an intraventricular DiI injection prior to injury. DiI and nestin-immunoreactivity is shown in the same sections, and GFAP-immunoreactivity in an adjacent section in (A-F). The approximate delineation of the injured area is indicated by the broken line in (D). (G) shows DiI (red) and GFAP-immunoreactivity (green) in the dorsal funiculus 2 weeks after the lesion. A yellow signal indicates co-localization of DiI and GFAP-immunoreactivity. (H) Confocal laser scanning microscope visualization of DiI and GFAP-immunoreactivity in the scar tissue 2 weeks after injury. Two GFAP-immunoreactive DiI labeled cells are indicated by arrowheads, and a DiI labeled cell which does not show any detectable GFAP is indicated with an arrow.

Figure 7A:
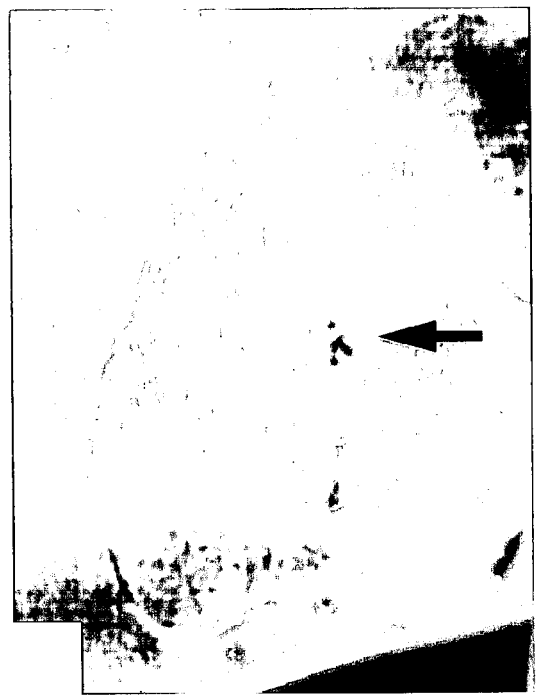
FIG. 7 discloses transplantation of purified of stem cells derived from transgenic animals.
Figure 7B:
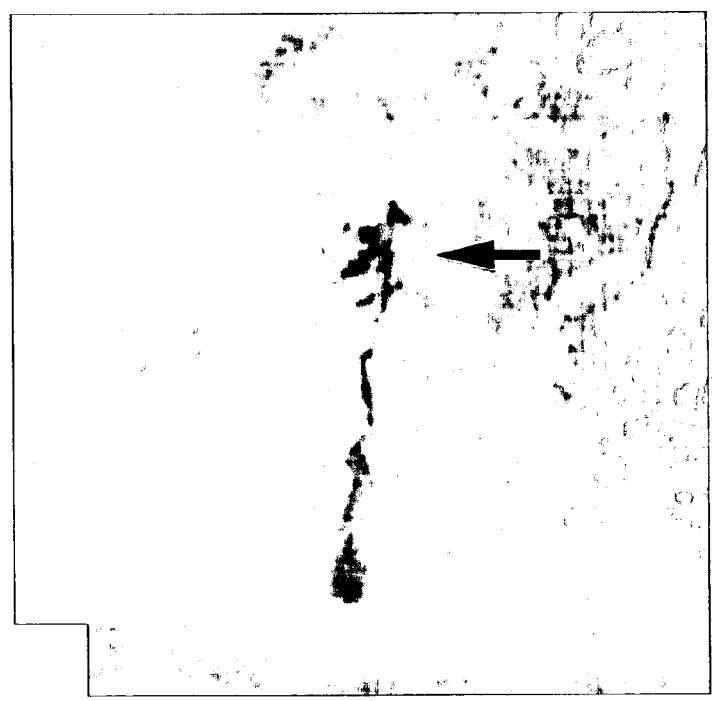

FIG. 7: Transplantation of Ependymal Neural Stem Cells

Transplantation of purified stem cells derived from transgenic mice expressing LacZ to the striatum of adult rats. The arrows point to a group of grafted cells. (B) shows a detail from (A).

Figure 8:
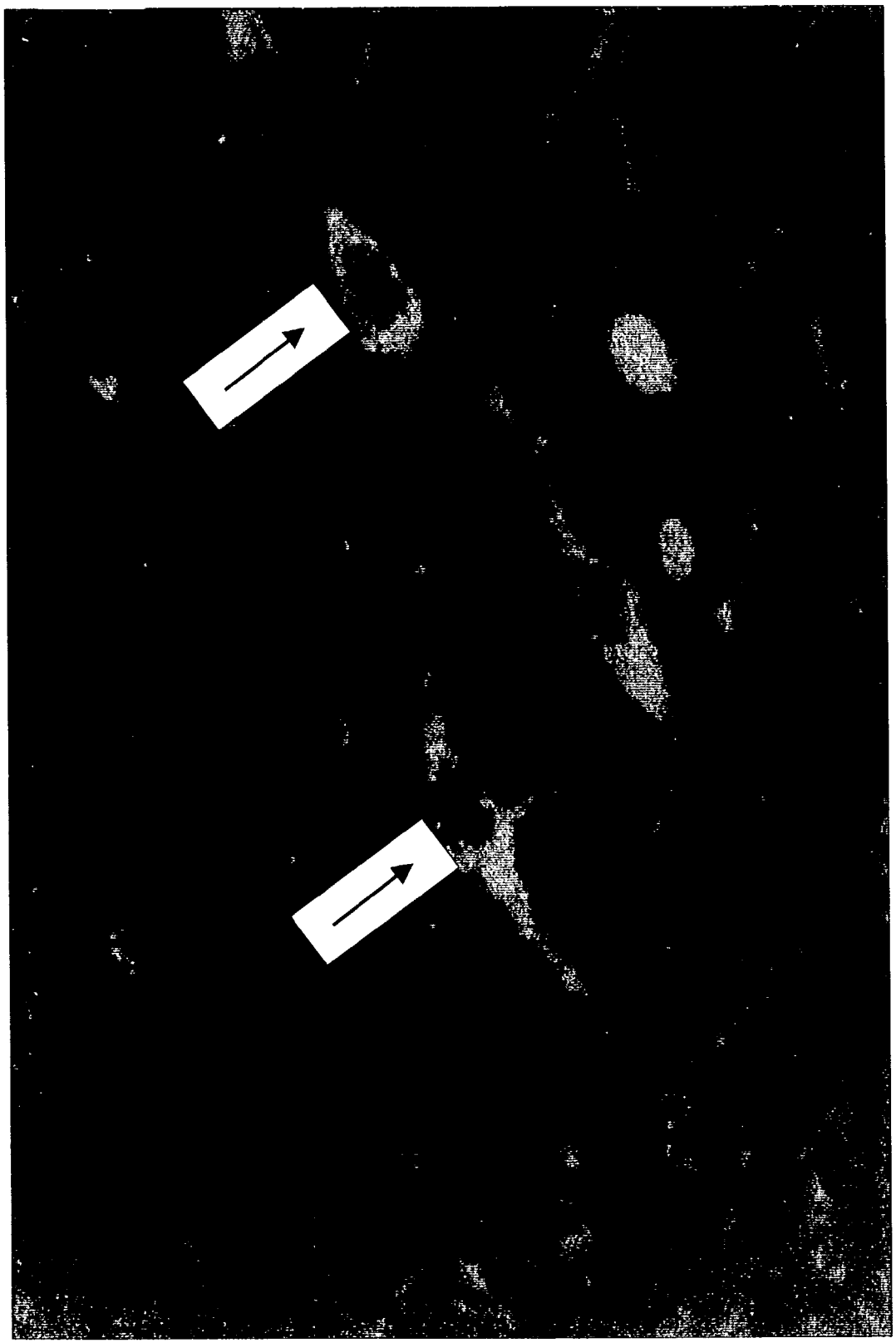
FIG. 8 shows the generation of neurons in substantia nigra from stem cells in the adult mouse.

FIG. 8: Generation of Neurons in Substantia Nigra from Stem Cells in the Ependymal Layer in the Adult Rat.

Microphotograph of nigral tyrosine hydroxylase-positive neurons (green) in substantia nigra pars compact also labeled with DiI (red) in rodents after administration of this fluorescent dye to the adult animal four months earlier. Arrows point at two nigral dopamine neurons containing the fluorescent marker labeling ependymal, neural stem cells.

Figure 9:
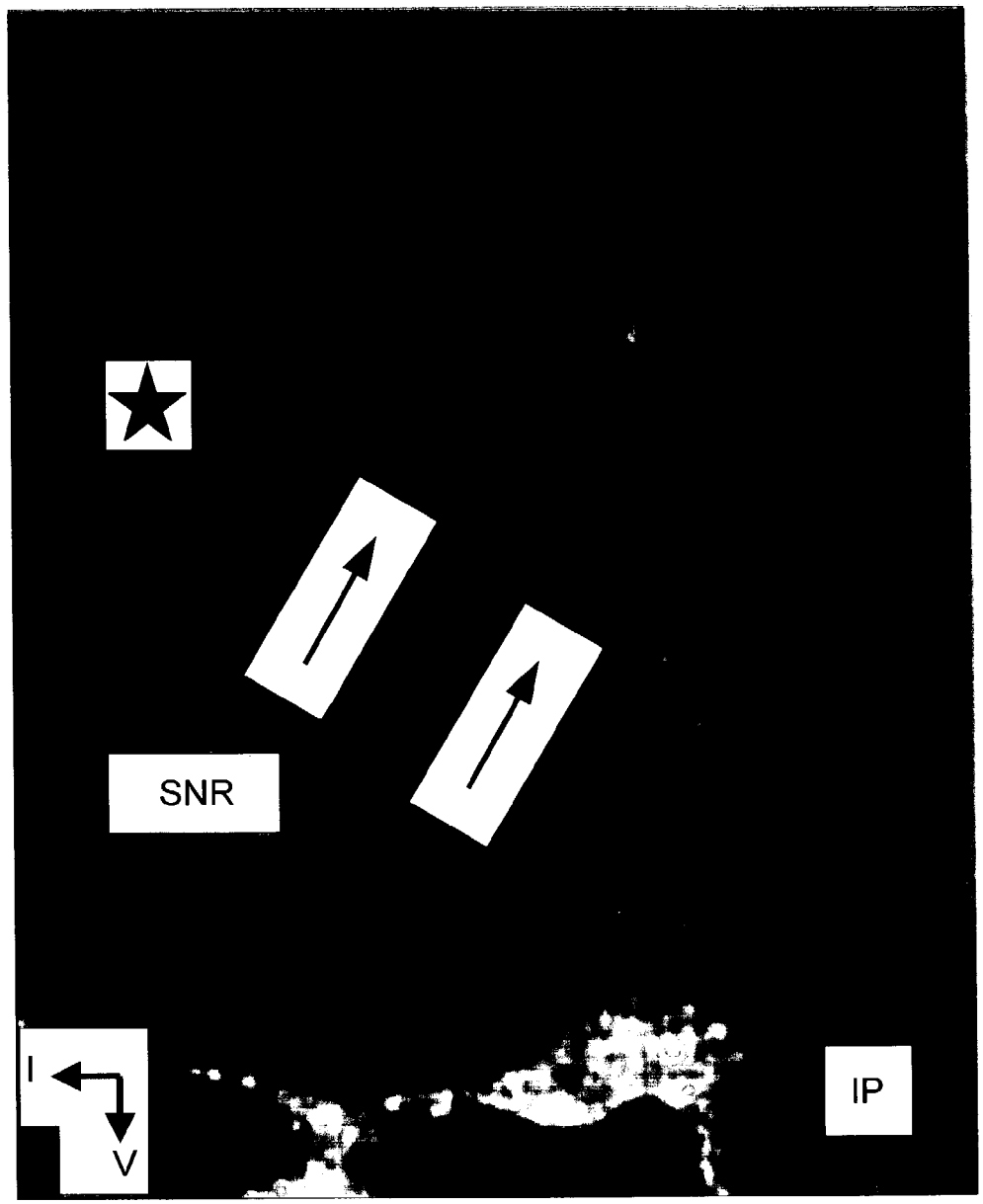
FIG. 9 illustrates migratory streams of stem cells or their progeny in the midbrain.

FIG. 9: Migratory Streams of Stem Cells from the Ependymal Layer or Their Progeny in the Mouse Midbrain.

Arrows point at the ventromedial migratory streams (red cells) of the DiI labeled ependymal cells that reach the medial substantia nigra pars compact (*). SNR=substantia nigra pars reticulata, IP=Interpeduncular nucleus. Arrows show lateral (l) and ventral (v) directions. Several pathways reaching rostral, caudal, medial and lateral parts of substantia nigra pars compact respectively were identified. In addition to the illustrated ventromedial stream, a dorsolateral and a midline stream were identified.

Figure 10:
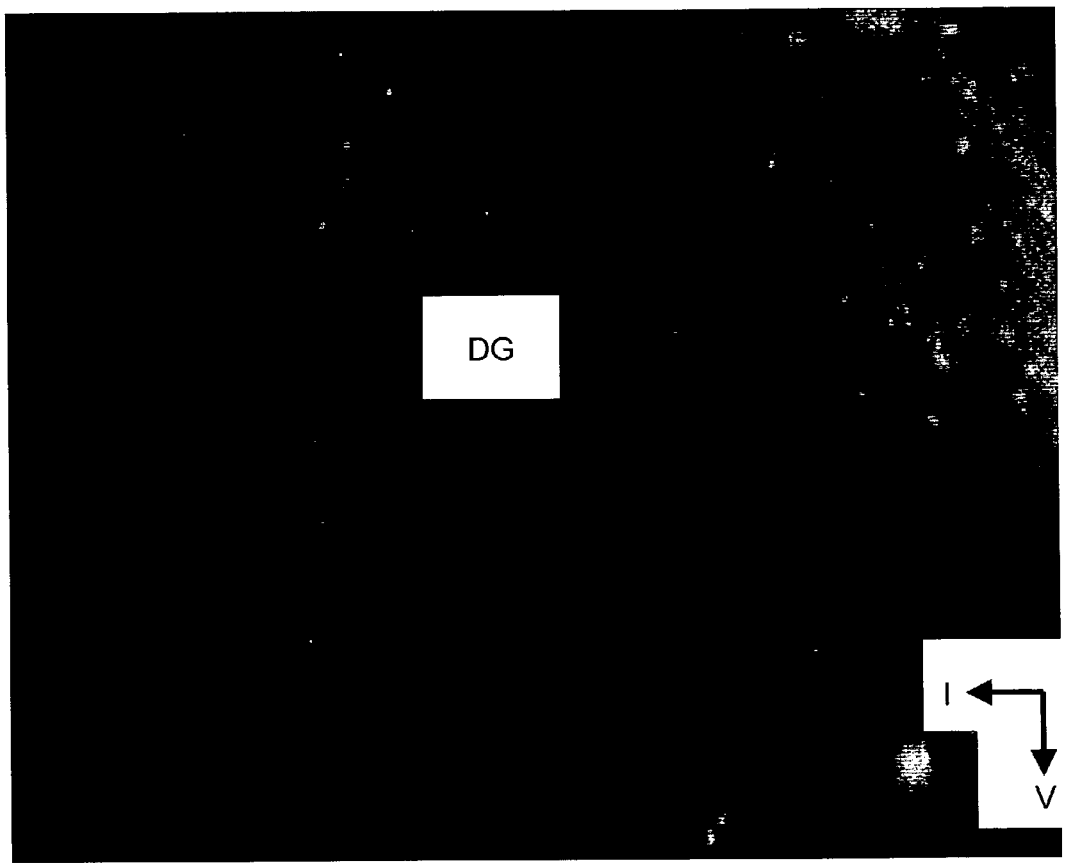
FIG. 10 discloses the generation of neurons in hippocampus from stem cells localized in the ependyma.

FIG. 10: Generation of Neurons in Mouse Hippocampus from Stem Cells Localized in the Ependymal Layer.

Microphotograph illustrating that the DiI labeled ependymal cells or their progeny migrate to the granule cell layer of the dentate gyrus (DG) of hippocampus. Arrows show lateral (l) and ventral (v) directions.

The following examples are presented only as illustrating the invention as defined by the claims and are in no way intended to limit the scope thereof. All references made below and elsewhere in the present disclosure are hereby included herein by reference.

EXAMPLES

Labeling of Ependymal Cells and their Progeny In Vivo

To test whether neurons may be generated from ependymal cells, we injected the fluorescent label DiI or a replication deficient adenovirus expressing the reporter-gene LacZ into the lateral ventricles of adult rats or mice. Male Sprague-Dawley rats weighing 280-320 g or male C57BL/6 mice weighing 25-30 g were anaesthetized with chloral hydrate (400 mg/kg). Unilateral stereotaxic injections of 10 μl (rats) or 3 μl (mice) of 0.2% w/v DiI (Molecular Probes) in DMSO or 50 μl adenovirus solution (containing $10^9$ plaque forming units) were made 0.9 mm (rats) or 0.5 mm (mice) posterior and 1.4 mm (rats) or 0.7 mm (mice) lateral to Bregma and 4 mm (rats) or 2 mm (mice) below the dura mater into the lateral ventricle. The injections resulted in specific labeling of the ependymal layer throughout the ventricular system; no labeling was seen in the subventricular zone nor in the brain parenchyma (FIG. 1). Thus, this method makes it possible to specifically follow the fate of the labeled ependymal cells and their progeny. Analysis of the distribution of DiI revealed an increasing number of labeled cells in the rostral migratory stream (Goldman et al., Trends Neurosci. 21:108), and after 10 days the first DiI labeled neurons were seen in the olfactory bulb, a region where new neurons are added continuously in adult mammals (FIG. 2). Similarly, in animals injected with the adenovirus, LacZ expressing cells were found in the olfactory bulb from 10 days after the injection, albeit at much lower numbers than in the DiI injected animals as expected since the adenovirus is replication deficient and the label will thus only be inherited by a subset of the progeny of the infected cell (FIG. 2). LacZ expression was detected with X-gal staining as described (Park et al., EMBO J. 16:3106).

Identification and Localization of Ependymal Neural Stem Cells by Culturing Labeled Ependymal Cells The specific labeling of ependyma in vivo may be used to test whether the labeled cells have stem cell properties in vitro. After an injection of DiI (described above), rats were killed with $CO_2$, their brains removed and kept in ice-cold PBS. The lateral walls of the lateral ventricles were dissected out. The tissue was minced with scissors, shifted to 4 ml of dissociation medium (0.075% collagenase type 1 (Worthington), 0.075% hyaluronidase (Sigma), 2000U DNAse I in 4 ml 0.2M PIPES (Sigma) and incubated at 37° C. for 30 min. Mechanical dissociation by gentle successive trituration through a 5 ml and 1 ml Pasteur pipette was followed by leaving the suspension for 2 min, allowing larger fragments to settle to the bottom. Then the supernatant was passed through a 40 μm mesh (Falcon). To the filtered suspension, 4 ml of cold medium (DMEM/F12) was added. Cells were spun down at 200 g for 4 min. The supernatant was removed, the pellet resuspended in 10 ml sucrose solution (0.9M in 0.5×HBSS) and centrifuged for 10 min at 750 g. The supernatant was removed and the pellet resuspended in 2 ml of culture medium, placed on top of 10 ml 4% BSA in EBSS solution and centrifuged at 200 g for 7 min, followed by a washing step in DMEM/F12. The culture medium was made of: 0.5 ml L-glutamine, 0.75 ml 1M HEPES (15 mM), 50 μl 20 μg/ml EGF (20 ng/ml), 1 ml B27 supplement, 0.5 ml 100× penicillin/streptomycin stock and, finally, DMEM-F12 medium to a total volume of 50 ml. Cell cultures were maintained at 37° C., 5% $CO_2$ in a humid atmosphere.

Under these conditions, characteristic spheroid cell aggregates of undifferentiated cells were formed in the cultures. These cell aggregates derive from a single stem cell and thus represent a clone of cells. Of these spheres, 88.6±1.20% and 89.0±1.23% from lateral ventricle and spinal cord, respectively, were clearly DiI labeled (mean from 5 independent experiments±SEM). DiI labeled spheres were collected and dissociated to single cells. Many of these cells formed new spheres, and when induced to differentiate by adding serum to the medium, most of these secondary spheres generated neurons, astrocytes and oligodendrocytes. Generation of differentiated progeny was demonstrated by immunohistochemical labeling with the following cell type specific antibodies: anti-glial fibrillary acidic protein (Dako) for astrocytes, Tuj1 (Babco) for neurons and O4 (Boehringer Mannheim) for oligodendrocytes. These experiments identify a useful method to study ependymal cells in vitro and demonstrate that ependymal cells have self renewal capacity and that they are multipotent, i.e. they are bona fide stem cells.

Purification of Ependymal Neural Stem Cells by Cell Sorting

We have found that Notch1 protein, a cell surface receptor expressed in the nervous system during embryonic development (Kopan et al., Trends Genet. 13:465), is selectively expressed in ependymal cells but not in subventricular zone cells in the adult rat brain and spinal cord (FIG. 3). We took advantage of this selective expression of Notch1 to isolate ependymal cells from acutely dissociated lateral ventricle wall and spinal cord tissue by magnetic sorting with Notch1 antiserum. For magnetic sorting, cells were collected as above and resuspended in 100 µl culture medium of the above defined composition, 1 µl of rabbit antiserum raised against Notch1 was added and incubated at 4° C. for 20 min. Subsequently, cells were washed with 6 ml of DMEM/F12, the pellet was resuspended in 100 µl of culture medium and 30 µl of pre-washed (with 0.5% BSA in PBS) magnetic bead-conjugated anti-rabbit antiserum ($1.8-2.1 \times 10^7$ beads, Dynal) was added and incubated for 20 min at 4° C. with occasional shaking. After incubation, 2 ml of culture medium was added, the suspension transferred into a 2 ml Eppendorf tube, placed in a Dynal magnetic separator and left for 2 min. The supernatant was collected in a 35 mm uncoated Nunc dish ('wash' fraction), then the magnet was removed from the separator, 2 ml culture medium (as defined above) was added to resuspend the bead-cell suspension and the magnetic separation step was repeated. The supernatant was again transferred to a culture plate. After removal of the magnet, 2 ml of culture medium were added, the remaining cells resuspended and transferred to a 35 mm uncoated Nunc dish. Throughout the whole procedure, all solutions and the cell suspensions were kept cold. Cell cultures were maintained at 37° C., 5% $CO_2$ in a humid atmosphere. Culture medium (composition as described above) was renewed every 3-4 days. Cells which had magnetic beads attached (sorted) or not (wash fraction) were then cultured and assayed for the presence of stem cells. Neurospheres started to appear around day 4-5 after isolation. In experiments where the cells had been sorted with the Notch1 antiserum, but not in experiments where the Notch1 antiserum was omitted, the majority of spheres formed in the sorted fraction (FIG. 3). When spheres formed in the Notch1 sorted fraction were dissociated they formed secondary spheres which were multipotent corroborating that ependymal cells are neural stem cells.

In other experiments, in vivo labeling of ependymal cells (see above) with DiI was followed by fluorescence activated cell sorting (FACS) or manual picking of fluorescent cells and resulted in highly enriched cultures of ependymal cells.

Ependymal Cells have a Slow Proliferation Rate and Generate a Transit Amplifying Precursor Population Previous studies, based on the lack of incorporation of labeled nucleotides after a single or a few injections, have indicated that ependymal cells do not proliferate in adult mammals. A characteristic feature of stem cells is that they proliferate slowly or rarely and administration of labeled nucleotides over long time periods have been used to identify slowly cycling stem cells in other tissues. It is thus likely that a slow proliferation rate of ependymal cells, which one would expect if they are stem cells, would be missed if analyzed by a single or a few injections of labeled nucleotides.

In order to characterize the proliferation of ependymal cells, we supplied the thymidine analogue 5-bromo-2'-deoxyuridine (BrdU, Sigma) continuously over long time periods. Rather than doing repeated injections, we administered BrdU to adult mice through; the drinking water over a two to six week period before analysis. To achieve long term labeling of the mouse brain, we added 1 mg/ml BrdU to the drinking water of mice. The water was exchanged twice a week and protected from light with aluminum foil. BrdU was efficiently taken up through the intestine, and resulted in labeling of ependymal cells lining the lateral walls of the lateral ventricles. Ependymal cells lining the roof and the medial wall of the lateral ventricles were rarely labeled, corresponding to the lateral wall being the most active neurogenic region. Very large numbers of BrdU labeled cells were present in the subventricular zone (FIG. 4). The labeled cells in the subventricular zone were often grouped in tight cell clusters, giving the impression of being a clone of cells (FIG. 4). Strikingly, in many cases such a cell cluster was located in close proximity to a labeled ependymal cell (FIG. 4). The proliferating precursor cells migrate closely together in the subventricular zone to the antero-lateral tip of the lateral ventricle where they enter the rostral migratory stream. The spatial relationship between a labeled ependymal cell and a cluster of subventricular zone cells was in the vast majority of cases so that the subependymal cells were shifted toward the rostral migratory stream in relation to the labeled ependymal cell (FIG. 4).

The fact that stem cells have a low proliferation rate has been used to localize stem cells in other tissues. When labeled nucleotides are administered over prolonged time periods, both rapidly and slowly proliferating cells will be labeled. By letting the animals survive for a period after the administration of the labeled nucleotide, rapidly proliferating cells will be given time to dilute the label by continued divisions or by migrating away. Therefore, only slowly proliferating cells will retain the label with time. We analyzed animals which had received BrdU continuously over a two to six week period followed by 2 weeks without BrdU. In these animals, very few labeled cells were seen in the subventricular zone, indicating that the vast majority of cells had diluted the label by repeated divisions or migrated away (FIG. 4). However, a substantial number of ependymal cells were still labeled (FIG. 4).

We next studied the proliferation of spinal cord ependymal cells. A substantial number of ependymal cells lining the central canal were labeled after prolonged administration of BrdU through the drinking water (FIG. 5). In contrast to in the lateral ventricle subventricular zone, few labeled cells were seen just outside the central canal ependyma (FIG. 5). However,the few labeled cells that were seen close to the central canal often resided in close proximity with a labeled ependymal cell, suggesting that this cell may derive from the ependyma (FIG. 5).

A Quantitative Method Analyzing Neurogenesis In Vivo in a Defined Brain Region such as Substantia Nigra Pars Compact in the Midbrain Several unpublished data from the present inventors have prompted them to postulate that the region of the brain where dopamine neurons die in Parkinson's disease, i.e. substantia nigra (Date, Brain Res. Bull. 40:1) represents a new region where a continuous turnover of neurons is present. State of the art stereological cell counting techniques in situ have been utilized and further developed (Gundersen et al., APMIS 96:857; Janson et al., Neuroscience 57:931) and the total number of nigral neurons in young and aged mice, as well as the total number of apoptotic neurons in the same region, analyzed. Briefly, the present inventor's unpublished results (Janson et al.) indicate that young and aged mice have the same number of nigral dopamine neurons, although a low number of neurons die spontaneously through apoptosis. At the same time the present inventors have found that nestin, a marker for neuronal progenitor cells as described above, is present in a subpopulation of nigral neurons (unpublished data, Janson et al.). Taken together these data indicate the possibility of a continuous neurogenesis in balance with neuronal apoptosis, i.e. neuronal turnover, which is described below. The quantitative method allows in vivo screening of substances enhancing neurogenesis and/or neuronal migration.

Adult rats and mice were given DiI through intraventricular injections as described in the example above. At various time intervals after the injection (hours-months), the animals were transcardially perfused with 15 ml 0.9% saline, followed by 50 ml of +4° C. 4% (w/v) paraformaldehyde and 0.4% (v/v) picric acid in 0.1 M phosphate buffered saline, pH 6.9, during 5 min. After brain removal, the tissue was fixed for an additional 90 minutes in the same fixative and cryoprotected in buffered sucrose (10% for 24 h, 30% for 2 days) at +4° C. The entire midbrain was cut with a cryostat using a systematic, uniform random sampling design, where 40 µm thick frontal sections were taken to six parallel rostrocaudal series. One series of sections was kept in 0.1 M PBS and the fluorescent signal was immediately converted to a permanent diaminobenzidine (DAB) signal using a modified previously described protocol (Singleton et al., J. Neurosci. Meth. 64:47). Thus, the sampled freshly cut free-floating sections were immersed for 10 min. in 1% $H_2O_2$ in 0.1 M Tris (pH 8.2) and then washed in buffer alone. Then the tissue was pre-incubated in the dark for 60 min. at +4° C. with filtered DAB (1.5 mg/ml of Tris buffer pH 8.2), rinsed in Tris buffer and then mounted on a glass slide and covered with fresh DAB solution, which was replaced with fresh solution every 30 min. during the photoconversion process. On each sampled slide substantia nigra was identified and the section was irradiated with ultraviolet light utilizing a 10× objective and a rhodamine filter in an epifluorescence microscope (Nikon). The photoconversion process was carefully evaluated and when all the fluorescent signal in substantia nigra was visualized with the brown DAB product, the sections were immunohistochemically labeled with a marker (Vector SG, Vector) for dopamine neurons (tyrosine hydroxylase) utilizing the avidin-biotin-immunoperoxidase system (Vector) (Janson et al., Neuroscience 57:931). The five parallel series of sections were instead stored in 30% sucrose in 0.1 M PBS at −20° C. until they were processed for immunohistochemistry and analyzed in a confocal laser scanning microscope utilizing several markers for glia and neurons (with appropriate controls) to determine the neuronal phenotype of the DiI labeled cells in substantia nigra pars compact (FIG. 8).

Quantitative estimates of the total number of TH immunoreactive cell bodies counterstained with cresyl violet (TH/CV+ neurons) as well as TH immunoreactive cell bodies also containing DiI label were made in the bilateral SNc. Neuronal counts were determined using coded sections and a stereological technique, the optical fractionator (Janson et al., Neuroscience 57:931). Briefly, the unbiasedly sampled sections in rostrocaudal order were analyzed with a CAST-Grid system (Computer Assisted Stereological Toolbox, Olympus, Albertslund, Denmark), which consists of a video camera on an Olympus BH2 microscope with a motorized specimen stage and a microcator to monitor movements in the z-axis (Heidenhain, Traunreut, Germany); both are linked to a PC with GRID software and a high resolution monitor. After encircling the SNc area in each sampled section at low-magnification, the analysis was performed at high magnification (100× oil immersion, numerical aperture 1.4). This allowed a clear visualization of individual cells in the densely populated encircled area as the focus moved through the tissue, which was optically dissected into thin slices and assessed by the microcator with a resolution of 0.5 µm. A computerized, uniform, systematic random sampling of small volumes (extending. 6-9 µm along the thickness of the section) was carried out; neurons with their nucleoli inside the sampling volume that fulfilled the stereological criteria were counted in a known fraction of the entire nigral volume. As described earlier (Chan et al., J. Pharmacol. Exp. Ther. 280:439), nigral neurons were counted if they showed both Nissl stained perikarya and TH immunoreactivity within the cell body and/or its dendrites. In the series of sections where the DiI signal was photoconverted, TH+ neurons containing DiI were counted (evaluation at 3,600×). The coefficient of error for each estimate of the total number of labeled neurons in different categories was determined. The obtained counts are independent of any dimensional changes in the tissue during processing such as shrinkage, which was determined along the z-axis. The total number of nigral dopamine neurons at various time points (a few hours to 60 days) were plotted against time, and from the regression curve ($r^2$=0.97) 175 new neurons were found to be generated each week in this brain region, which is around one percent of the total number of nigral dopamine neurons in the mouse.

Several migratory streams of DiI labeled cells were characterized as they reached different parts of substantia nigra pars compact (not known or described before, FIG. 9). With the application of a modified protocol for cell counting using a fluorescent microscope, the total number of cells in each of the defined migratory streams is being determined. The interpretation that the DiI labeled neurons were indeed newly generated was confirmed with BrdU labeling in animals receiving chronic administration via drinking water (1 mg/ml, see example above). Furthermore, evidence that the 'new' neurons were functional and developed appropriate neuronal processes was supported by the finding of DiI in some of the TH+ striatal nerve terminals at late, but not at early survival times.

The Progeny of Labeled Ependymal Neural Stem Cells Include Neurons in Several Brain Regions and of Various Phenotypes Utilizing the in vivo fluorescent labeling protocol described above, we identified several regions of the brain where DiI labeled cells were identified as neurons. These regions include several parts of the hippocampus, including the granular layer of the dentate gyrus (FIG. 10), cortical layers and subcortical structures such as the presumably gamma-aminobutyric-acid (GABA)-containing neurons in the subthalamic and substantia nigra pars reticulata regions as well as serotoninergic neurons in the raphe brain nuclei.

Generation of Genetically Modified Stem Cells In Vitro

Genetically engineered stem cells were generated by culturing the stem cells as above, and then transfecting them with expression plasmids or viral vectors. For each transfection, 4 µg DNA (the method was established using the plasmid CMV-GFP from Clontech, encoding the-green fluorescent protein (GFP) as a reporter) was added to 200 µl culture medium (defined above) in a 12×75 mm conical tube (15 ml) and gently mixed. In a second conical tube 15 µl Lipofectamine reagent was added into 200 µl culture medium and vortexed gently. The two solutions were then combined by adding the second to the first and incubated at room temperature 45 min. to allow DNA-liposome complexes to form. Then 1.6 ml culture medium was added to the tube with the DNA-liposome complexes and this solution was overlaid on the cells (which had the majority of their medium carefully removed). Cells were incubated 12 hours and then the medium was replaced with the regular culture medium without DNA. GFP detection was performed in a fluorescence microscope 48-72 hours post-transfection. These stem cells could be clonally expanded to generate spheres of undifferentiated genetically modified stem cells.

Altered Gene Expression in Stem Cells In Vivo

The feasibility of altering gene expression in stem cells in vivo was done by injecting a replication deficient adenovirus carrying the reporter-gene LacZ under the control of the RSV promoter into the lateral ventricles as described above. X-gal staining (described above) demonstrated expression of a reporter-gene in ependymal stem cells, and thus the feasibility of altering gene expression in stem cells. Stem cells carrying genes driving the expression of nerve growth factor, glial cell-line-derived neurotrophic factor (neuronal survival factor), bc1-2 (a gene which will promote the survival of the stem cells) and nurr1 (which may promote the generation of dopaminergic neurons from stem cells) are being generated.

The Use of Stem Cells from Transgenic Animals

We have found that it is possible to culture stem cells from transgenic animals. For these studies we have used mice carrying the LacZ gene in their genome (Zambrowicz et al. Proc. Natl. Acad. Sci. USA., 94:3789). These mice express the transgene ubiquitously in all tissues (Zambrowicz et al. Proc. Natl. Acad. Sci. USA., 94:3789). Stem cells from these mice were purified and cultured as above. Strong transgene expression was revealed by X-gal staining as described above.

Manipulation of Stem Cell Proliferation and Differentiation by Traumatic Injury

In adult rats a laminectomy was performed at the mid thoracic level to expose the spinal cord, and the dorsal funiculus was cut transversely with microsurgical scissors, and the lesion was subsequently extended rostrally by a superficial longitudinal incision in the dorsal funiculus. In other animals, a hole was drilled in the skull and a needle was inserted into the brain tissue to induce an injury. In some animals the ependymal cells had been labeled 1-10 days before the injury by a DiI injection as described above.

Quantification of the proportion of ependymal cells that proliferate at different time points after an incision in the dorsal funiculus revealed an almost 50-fold increase 1 day after the injury compared to uninjured animals (FIG. 5). After the first day, the proliferation gradually declined toward normal within one month (FIG. 5). Likewise, ependymal cell proliferation was greatly increased in the wall of the lateral ventricle following brain injury.

In animals in which the ependymal cells were labeled by a DiI injection prior to the spinal cord or brain injury, an increasing number of DiI labeled cells were seen progressively further outside the ependymal layer over the first four weeks after the injury (FIG. 6). DiI labeled cells were abundant in the forming scar tissue within one week after the lesion and persisted there for at least one year. Within the scar tissue forming at the injury the vast majority of the DiI-labeled cells showed immunoreactivity to glial fibrillary acidic protein, an astrocyte marker, indicating that the majority of progeny from ependymal cells had differentiated to astrocytes (FIG. 6). However, neuronal markers were not found in the DiI labeled cells indicating that the signals required for neuronal transformation of the stem cells were not present in this animal model.

Chemicals Increasing Neurogenesis in Substantia Nigra Pars Compact in the Midbrain Separate mice were given the 1-methyl-4-phenyl-1,2,3,6-tetrahydropyridine (MPTP, RBI, Natick, MA, USA) (40 mg/kg diluted in physiological saline, sc.). This substance is known for its selective neurotoxic actions on dopamine neurons in the midbrain causing parkinsonism in humans and experimental animals (Langston et al., Science 219:979, Heikkila et al., Science 224:1451). However, the molecule also has structures in common with compounds known to act as neuroprotective agents in animal models of Parkinson's disease, e.g. nicotine (Janson et al., Neuroscience 57:931).

In our experiments animals were given MPTP or vehicle and the time course of changes in the number of DiI+ nigral dopamine cells or in the staining pattern of the migratory streams of DiI+ cells moving towards this brain region were analyzed (see above, quantitative method to study neurogenesis in substantia nigra pars compact in the midbrain after labeling of ependymal cells). The treatment led to higher numbers of TH+/DiI+ nigral neurons indicating an increased neurogenesis. The total number of nigral dopamine neurons at various time points (a few hours to 2 months) were plotted against time, and from the regression curve ($r^2$=0.744) the number of new neurons found to be generated each week in this brain region was increased with 24% compared to animals treated with vehicle alone. Also, the migratory streams of DiI+ cells in the midbrain appeared more pronounced in animals treated with MPTP, which can be analyzed quantitatively using the modified stereological method described above.

Transplantation of Ependymal Stem Cells

Ependymal stem cells from the brain or spinal cord of Rosa26 transgenic mice were purified and cultured as above. Spheres of undifferentiated stem cells from these mice were transplanted to the striatum of adult rats, by stereotaxic injection of spheres in 15 µl of their culture medium (described above). The animals were sacrificed 2 days later and the brains sectioned and analyzed for the presence of LacZ expressing cells deriving from the Rosa26 mice by X-gal staining as described above. The grafted cells were scattered in the tissue close to the insertion canal. These cells often had several processes (FIG. 7).

Various publications are cited herein, the disclosures of which are incorporated by reference in their entireties.

The present invention is not to be limited in scope by the specific embodiments described which are intended as single illustrations of individual aspects of the invention, and functionally equivalent methods and components are within the scope of the invention. Indeed various modifications of the invention, in addition to those shown and described herein will become apparent to those skilled in the art from the foregoing description and accompanying drawings. Such modifications are intended to fall within the scope of the appended claims.

We claim:

1. A method of determining whether a test compound is a proliferation-inducing agent, said method comprising:
    (a) contacting an ependymal neural stem cell with the test compound; and
    (b) determining the proliferation of the ependymal neural stem cell, wherein if the proliferation of the ependymal neural stem cell is increased in the presence of the test compound as compared to the absence of the test compound, the test compound is identified as a proliferation-inducing agent.

2. A method of determining whether a test compound is a proliferation-inhibiting agent, said method comprising:
    (a) contacting an ependymal neural stem cell with the test compound; and
    (b) determining the proliferation of the ependymal neural stem cell, wherein if the proliferation of the ependymal neural stem cell is decreased in the presence of the test compound as compared to the absence of the test compound, the test compound is identified as a proliferation-inhibiting agent.

3. The method of claim 2, wherein the method further comprises contacting the ependymal neural stem cell with a proliferation-inducing agent.

* * * * *